(12) United States Patent
Freiburger et al.

(10) Patent No.: US 7,912,264 B2
(45) Date of Patent: Mar. 22, 2011

(54) MULTI-VOLUME RENDERING OF SINGLE MODE DATA IN MEDICAL DIAGNOSTIC IMAGING

(75) Inventors: Paul Donald Freiburger, Seattle, WA (US); Mervin Mencias Smith-Casem, Renton, WA (US); Liexiang Fan, Sammamish, WA (US); Andrzej Milkowski, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 879 days.

(21) Appl. No.: 11/890,124

(22) Filed: Aug. 3, 2007

(65) Prior Publication Data
US 2009/0036749 A1   Feb. 5, 2009

(51) Int. Cl.
*G06K 9/00* (2006.01)
*A61B 8/00* (2006.01)
(52) U.S. Cl. .................... 382/128; 382/154; 600/441
(58) Field of Classification Search .................. 382/100, 382/128, 129, 130, 131, 132, 133, 134, 154, 382/162–167, 168, 181, 214, 137, 160, 274, 382/275, 276, 285, 305; 600/447, 441, 300, 454; 378/4, 20, 21
See application file for complete search history.

(56) References Cited

U.S. PATENT DOCUMENTS

| 5,623,928 | A | * | 4/1997 | Wright et al. ................. 600/447 |
| 5,720,291 | A |   | 2/1998 | Schwartz |
| 5,720,294 | A | * | 2/1998 | Skinner ........................ 600/300 |
| 5,860,924 | A | * | 1/1999 | Quistgaard .................... 600/441 |
| 6,280,387 | B1 | * | 8/2001 | Deforge et al. ............... 600/454 |
| 6,755,787 | B2 | * | 6/2004 | Hossack et al. ............... 600/447 |

* cited by examiner

*Primary Examiner* — Seyed Azarian

(57) ABSTRACT

Separate renderings are performed for data of a same medical imaging mode. The data is processed differently prior to rendering and/or rendered differently to enhance desired image information. For example, a same set of ultrasound B-mode data is rendered with opacity rendering and with maximum intensity projection or surface rendering. The surface or maximum intensity projection highlights strong transitions associated with bones. The opacity rendering maintains tissue information. Different sets of B-mode data may be separately rendered, such as one set processed to emphasize contrast agent response and another set processed to emphasize tissue. The separate renderings are aligned and combined. The combined rendering is output as an image.

18 Claims, 2 Drawing Sheets and imaging. In medical diagnostic ultrasound imaging, the same imag-
MULTI-VOLUME RENDERING OF SINGLE MODE DATA IN MEDICAL DIAGNOSTIC IMAGING

BACKGROUND

The present embodiments relate to volume rendering. In particular, medical data is volume rendered.

In medical diagnostic ultrasound imaging, the same imaging mode may be use to image different characteristics. For example, B-mode data may show tissue and bone. As another example, color Doppler flow mode may show velocity and power of fluid or tissue. For two-dimensional imaging, the different modes may be combined, such as Doppler velocity information being displayed as an overlay on B-mode tissue information.

For three-dimensional imaging, a single source of image information is typically used. For example, Doppler power or B-mode tissue information representing a volume is rendered to a two-dimensional display. However, using a single source of information may be less diagnostically useful.

Multiple modes of imaging may be used for three-dimensional rendering. For example, separate renderings are provided for B-mode and flow information. However, the resulting images may not provide the desired diagnostically useful information.

BRIEF SUMMARY

By way of introduction, the preferred embodiments described below include methods, systems, instructions, and computer readable media for volume rendering data in medical diagnostic imaging. Separate renderings are performed for data of a same imaging mode. The data is processed differently prior to rendering and/or rendered differently to enhance desired image information. For example, a same set of B-mode data is rendered with opacity rendering and with maximum intensity projection or surface rendering. The surface or maximum intensity projection highlights strong transitions associated with bones. The opacity rendering maintains tissue information. Different sets of B-mode data may be separately rendered, such as one set processed to emphasize contrast agent response and another set processed to emphasize tissue. The separate renderings are aligned and combined. The combined rendering is output as an image.

In a first aspect, a system for volume rendering data in medical diagnostic imaging is provided. A memory is operable to store at least one dataset representing a three-dimensional volume, each of the at least one dataset being from a same imaging mode. A processor is operable to volume render first and second two-dimensional representations of the volume from the at least one dataset. The processor is operable to combine the first and second two-dimensional representations into a combined two-dimensional representation. A display is operable to display the combined two-dimensional representation as an image. (1) The at least one dataset is first and second data sets from the same imaging mode with different processing, (2) the first and second two-dimensional representations are rendered differently, or (3) a combination of (1) and (2).

In a second aspect, a method for volume rendering data in medical diagnostic imaging is provided. A first three-dimensional representation is rendered from a first dataset of b-mode or flow mode type of ultrasound data. A second three-dimensional representation is rendered from the first or a second dataset of b-mode or flow mode ultrasound data. Both the first and second three-dimensional representations are rendered from a same one of the b-mode or flow mode types. The first and second three-dimensional representations are combined.

In a third aspect, a computer readable storage medium has stored therein data representing instructions executable by a programmed processor for volume rendering data in medical diagnostic imaging. The storage medium includes instructions for separately rendering from data of a single ultrasound mode, each separate rendering having different information from the data being relatively enhanced, and combining the separate renderings into a single view.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Data acquired a same mode is processed and displayed with multiple independent rendering paths. Each path is optimized separately to enhance different information. The separate renderings are then spatially aligned, and the resultant volumes are combined. The multiple volumes that make up the single displayed volume can be color-coded differently, stripped away separately, or manipulated in other manners that enhance the display of the different information extracted by the different rendering paths.

In one example embodiment, a volume is displayed which is a combination of two or more volume renderings that have been separately rendered. Each individual volume rendering enhances different information. The data is acquired from a single mode type. The datasets input to the renderer have at least one difference in content prior to rendering. Two or more volume renderings may be performed on data acquired from multiple acquisitions with the acquisitions being of the same mode type. Two or more volume renderings may be performed on data acquired from a single acquisition with at least one difference in data processing prior to rendering. The displayed volume may be manipulated in a manner that enhances the independent information content extracted by the independent renderer paths (e.g. stripping away layers, colorizing different sub-volumes differently, etc.). Other embodiments are possible.

Figure 1:
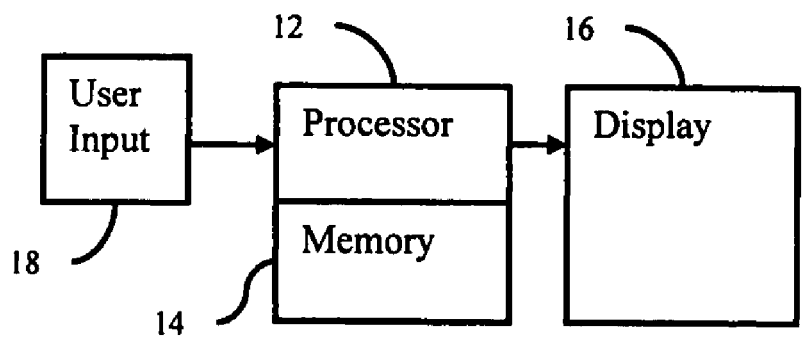
FIG. 1 is a block diagram of one embodiment of a system for volume rendering.

FIG. 1 shows a system for volume rendering data in medical diagnostic imaging. The system is capable of performing multiple rendering passes or parallel renderings with different data and/or rendering settings and combining the results. The system includes a processor 12, a memory 14, a display 16, and a user input 18. Additional, different, or fewer components may be provided. For example, a network or network connection is provided, such as for networking with a medical imaging network or data archival system.

The system is part of a medical imaging system, such as a diagnostic or therapy ultrasound, x-ray, computed tomography, magnetic resonance, positron emission, or other system. Alternatively, the system is part of an archival and/or image processing system, such as associated with a medical records database workstation or networked imaging system. In other embodiments, the system is a personal computer, such as desktop or laptop, a workstation, a server, a network, or combinations thereof for rendering three-dimensional representations.

The user input 18 is a keyboard, trackball, mouse, joystick, touch screen, knobs, buttons, sliders, touch pad, combinations thereof, or other now known or later developed user input device. The user input 18 generates signals in response to user action, such as user pressing of a button.

The user input 18 operates in conjunction with a user interface for context based user input. Based on a display, the user selects with the user input 18 one or more controls, imaging modes, types of rendering, rendering parameters, values, quality metrics, an imaging quality, or other information. For example, the user positions a cut-plane associated with a volume. As another example, the user selects rendering or color mapping. Other manipulations of data and/or renderings may be provided. In alternative embodiments, the processor 12 selects or otherwise controls without user input (automatically) or with user confirmation or some input (semi-automatically).

The memory 14 is a graphics processing memory, video random access memory, random access memory, system memory, cache memory, hard drive, optical media, magnetic media, flash drive, buffer, combinations thereof, or other now known or later developed memory device for storing data or video information. The memory 14 communicates with the processor 12.

The memory 14 stores data. Any type of data may be used for volume rendering, such as medical image data (e.g., ultrasound, x-ray, computed tomography, magnetic resonance, or positron emission). The rendering is from data distributed in an evenly spaced three-dimensional grid, but may be from data in other formats (e.g., rendering from scan data free of conversion to a Cartesian coordinate format or scan data including data both in a Cartesian coordinate format and acquisition format). The data is voxel data of different volume locations in a volume. The voxels are the same size and shape within the dataset. Voxels with different sizes, shapes, or numbers along one dimension as compared to another dimension may be included in a same dataset, such as is associated with anisotropic medical imaging data. The dataset includes an indication of the spatial positions represented by each voxel.

The memory 14 stores one or more datasets representing a three-dimensional volume for rendering. In one embodiment, a single dataset is stored. In another embodiment, two or more different datasets are stored.

The single or multiple datasets include data from a same imaging mode. For ultrasound, an imaging mode is a detection technique or other general mode of operation. For example, B-mode data corresponds to detection of intensity of received signals. The intensity or response may represent tissue, bone, contrast agent, or other structure. As another example, color Doppler mode corresponds to Doppler detection of receive signals, such as velocity, variance, and/or power. The color Doppler mode may output data representing fluid, contrast agents, moving tissue, or other moving structure. Other modes include parametric imaging modes. In parametric imaging mode, strain, strain rate, impedance or other strain characteristic of tissue is parameterized. Imaging modes may have a set or dedicated key on the user input 18 for designating the mode. Other imaging modes may be selected as an application.

For multiple datasets associated with a same imaging mode, the datasets may have been processed differently. For example in color Doppler mode, velocity estimation is different than power estimation. Different color mapping may be used. As another example, different filters may be applied to B-mode data to isolate contrast agent response from tissue response (e.g., harmonic and fundamental filtering). Different transmit or receive sequences and combinations may be used for B-mode information to isolate contrast agent and tissue information.

The dataset is provided in real-time with acquisition. For example, the dataset is generated by medical imaging of a patient. The memory 14 stores the data temporarily for processing. Alternatively, the dataset is stored from a previously performed scan. For different datasets, the datasets are acquired or formed from different scans of a patient. Alternatively, the different datasets are formed by different processing of data from a same scan of the patient. The different datasets may be stored separately or may be generated for rendering from a single stored dataset.

The processor 12 is a central processing unit, control processor, application specific integrated circuit, general processor, field programmable gate array, analog circuit, digital circuit, graphics processing unit, graphics chip, graphics accelerator, accelerator card, combinations thereof, or other now known or later developed device for rendering. The processor 12 is a single device or multiple devices operating in serial, parallel, or separately. The processor 12 may be a main processor of a computer, such as a laptop or desktop computer, may be a processor for handling some tasks in a larger system, such as in an imaging system, or may be a processor designed specifically for rendering. In one embodiment, the processor 12 is, at least in part, a personal computer graphics accelerator card or components, such as manufactured by nVidia, ATI, or Matrox.

The processor 12 is operable to volume render a two-dimensional representation of the volume from a dataset. The two-dimensional representation represents the volume from a given or selected viewing location. Volume rendering is used in a general sense of rendering a representation from data representing a volume. For example, the volume rendering is projection or surface rendering. In projection rendering, an average, minimum, maximum, or other combination of data along a ray or projection line may be used. Alpha blending may be used. The data may be weighted with opacity, shading, or other weights prior to or after combination. Maximum projection rendering may be similar to or represent a surface. For example, the intensity above a threshold or with a sufficient transition and closest to a viewing location is selected as the pixel value. Other surface rendering may be used.

The rendering algorithm may be executed efficiently by a graphics processing unit. The processor 12 may be hardware devices for accelerating volume rendering processes, such as using application programming interfaces for three-dimensional texture mapping. Example APIs include OpenGL and DirectX, but other APIs may be used independent of or with the processor 12. The processor 12 is operable for volume rendering based on the API or an application controlling the API. The processor 12 is operable to texture map with alpha blending, minimum projection, maximum projection, surface rendering, or other volume rendering of the data. Other types of volume rendering, such as ray casting, may be used.

The rendering algorithm renders as a function of rendering parameters. Some example rendering parameters include voxel word size, sampling rate (e.g., selecting samples as part of rendering), interpolation function, size of representation, pre/post classification, classification function, sampling variation (e.g., sampling rate being greater or lesser as a function of location), downsizing of volume (e.g., down sampling data prior to rendering), shading, opacity, minimum value selection, maximum value selection, thresholds, weighting of data or volumes, or any other now known or later developed parameter for rendering.

Two or more different two-dimensional representations of the volume are rendered. The different two-dimensional representations are formed by rendering from a same or different datasets. Different types of rendering and/or different rendering parameter values are used. Alternatively or additionally, different datasets are rendered with the same or different rendering parameter values. For example, datasets of data from a same imaging mode but different processing are rendered. Due to different datasets, different rendering, or both, different two-dimensional representations of a same volume or overlapping volumes are rendered.

For example, opacity rendering by opacity weighting (weighted average) data along projections is performed for one rendering, and maximum intensity projection rendering or surface rendering is performed for another rendering. The differences in rendering may emphasize different information in a dataset. For B-mode data, the different renderings may show bone (surface or maximum intensity) and tissue (opacity rendering) even with rendering from a same or single dataset.

In other examples, differences in the datasets used for rendering show different information with or without differences in rendering. Parametric information in B-mode, like elasticity or stiffness, may be color mapped differently than acoustic impedance (e.g., elasticity in red scale and impedance in gray scale). A dataset of contrast information in B-mode may be rendered using maximum intensity projection, and a dataset of tissue B-mode may be rendered with opacity rendering. Velocity and Power datasets of data in color Doppler mode may be rendered separately. Different color mapping may also be provided, such as power rendered using an orange/yellow tint map and velocity rendered using a red/blue tint map.

The two-dimensional representations may be further processed differently or the same. For example, the color mapping is applied to the data of the two-dimensional representation. Alternatively, the color mapping is applied as a difference in processing to the dataset representing the volume before rendering.

Two or more two-dimensional representations are combined. The renderings are aligned for combination. Each representation represents a same or overlapping volume. The renderings are from a same viewing location and to a same scale, or the representations are adjusted to account of spatial differences. The alignment is calculated from known spatial locations of the dataset. Alternatively or additionally, the datasets and/or the representations are aligned by correlation. A best or sufficient match associated with translation and/or rotation of data relative to other data (e.g., one representation relative to another representation) is found.

The aligned data is combined. The combination is averaging, maximum or minimum selection, or other combination. Weighted combination may be used. In one embodiment, alpha blending in an infinite impulse response is provided. In another embodiment, one of the samples for a given location is selected based on a criterion, such as a threshold in data intensity or opacity. Selection may allow favoring of one channel over another provided the one channel meets the criteria.

Data from the different representations representing the same projection, pixel, or region are combined. The result of the combination is a two-dimensional representation. The pixel values of at least some regions are a function of the values from the different representations. Filtering may be used to reduce any line artifacts of the combination.

Figure 3:
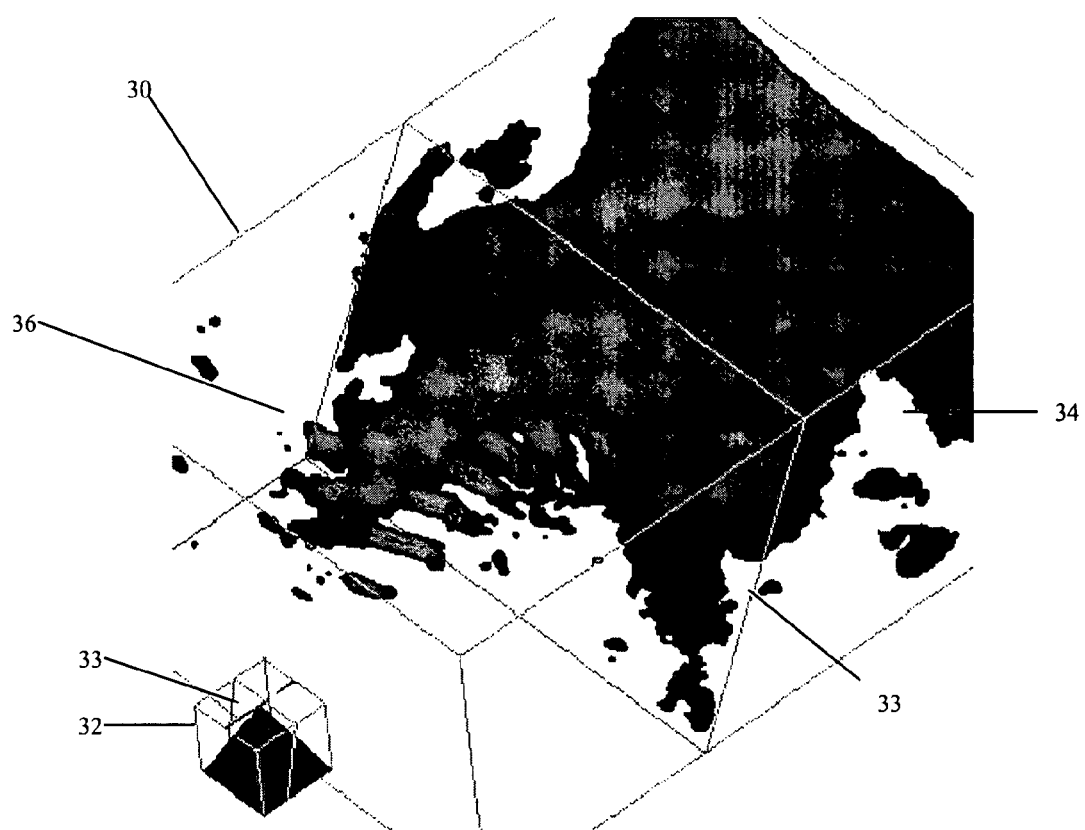
FIG. 3 illustrates an example image generated from separate renderings of B-mode data.

FIG. 3 shows one example of an image 30 of a representation formed from two renderings. The image 30 shows a same B-mode dataset rendered in different ways. The dataset is from one scan of a fetus. Maximum intensity projection enhances visualization of fetal skeleton, and opacity rendering enhances visualization of soft tissues. A graphics box 32 allows placement of a cut plane 33, separating a right portion 34 from a left portion 36. The right portion 36 includes data from both renderings. The left portion 36 includes data from the maximum intensity rendering. In a color version, the tissue may be mapped to a red/orange tint, and the bone mapped to gray tint. Alternatively, the selection criterion for the combination is the tissue rendering for the right portion 34 and the bone rendering for the left portion 36. Other combinations may be used.

Providing different two-dimensional representations may allow for independent manipulation. Changes to one dataset and/or rendering may be made without changes to the other dataset and/or rendering. Different changes may be made to the different renderings and/or datasets. For example, the datasets or two-dimensional renderings may be color mapped differently. The color scale used for one rendering or corresponding dataset may be changed. As another example, the cut plane 33 or other masking is altered to define the limits of one representation. The use of two renderer paths allows the soft tissue to be stripped away to better reveal the skeletal information underneath. Any user navigation may be provided, such as associating any user control with a default or selected one of the renderings.

The display 16 is a monitor, LCD, projector, plasma display, CRT, printer, or other now known or later developed devise for outputting visual information. The display 16 receives images or other information from the processor 12. The pixel values are received by the display 16 for generating an image. The display 16 displays the combined two-dimensional representation of the volume as an image. The image may include other information, such as a graphics box 32 and/or cut-plane 33.

The display 16 is part of a user interface. The user interface may provide for manipulation of the rendering and/or datasets.

The memory 14 and/or another memory stores instructions for operating the processor 12. The instructions are for volume rendering data in medical diagnostic imaging. The instructions for implementing the processes, methods, and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts, or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 2:
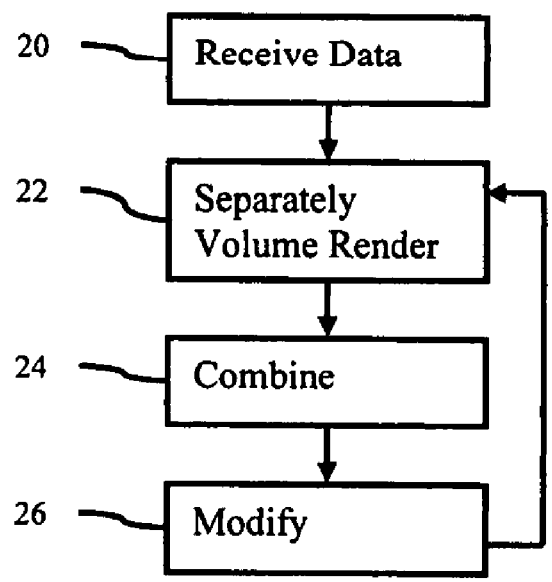
FIG. 2 is a flow chart diagram of one embodiment of a method for volume rendering data in medical diagnostic imaging.

FIG. 2 shows a method for volume rendering data in medical diagnostic imaging. The method is implemented by the system of FIG. 1 or another system. The acts of the method are performed in the order shown or other orders. Additional, different, or fewer acts may be provided. For example, act 26 is optional.

In act 20, data is received. The data is received in response to a request by the rendering system, in response to a user request, from another component, or otherwise received. The dataset is received from a memory, a scanner, or a transfer. In one embodiment, the data is received within an ultrasound imaging system by scanning a patient.

The received data includes one or more datasets each representing a volume. The datasets are isotropic or anisotropic. The datasets have voxels spaced along three major axes or other format. The voxels have any shape and size, such as being smaller along one dimension as compared to another dimension. The dataset for volume rendering is from any medical modality, such as computed tomography, magnetic resonance, or ultrasound.

In act 22, separate renderings are performed. The separate renderings are sequential or parallel renderings. In one embodiment, the renderings are from a same dataset. In another embodiment, the renderings are from different datasets. The different datasets are from a same scan, but with different processing, or from different scans of a patient.

The dataset or datasets for the rendering are from a same imaging mode. One or more datasets may include data from different modes of imaging, but the datasets include data from at least one mode of imaging common to the datasets (e.g., one dataset with B-mode data and another dataset with B-mode and color Doppler mode data). Data from a single ultrasound mode is separately rendered. Data from other modes may be included.

The separate renderings provide for two-dimensional representations with different information. By starting with data processed differently and/or by rendering differently, different information is relatively enhanced. The enhancement may be through the different processing to create or alter different datasets, resulting in different information in each dataset. The enhancement may be through selecting information in a dataset by differences in rendering. Different information is provided in the different two-dimensional representations, providing relative enhancement over other information.

In one embodiment, different rendering is provided. A same or different datasets are rendered differently. One or more rendering parameters are set different. Alternatively or additionally, different types of rendering are performed.

In another embodiment, different datasets are rendered. The different datasets include data from a same mode, but processed differently (e.g., different color maps).

One representation is rendered from a dataset. The dataset includes B-mode information, color Doppler information (e.g., velocity estimates), or data from another imaging mode. Any type of rendering may be used, such as opacity rendering. Another representation is rendered from the same or a different dataset. If separate datasets are used, the datasets both include data from a same imaging mode. The dataset includes B-mode information, color Doppler information (e.g., power estimates), or data from another imaging mode. Any type of rendering may be used, such as surface or maximum intensity projection rendering.

For rendering, the viewing parameters determine a view location. The view location is a direction relative to the volume from which a virtual viewer views the volume. The view location defines a view direction and/or distance from the volume. The view location may be within the volume. The viewing parameters may also include scale, zoom, shading, lighting, and/or other rendering parameters. User input or an algorithm defines the desired viewer location.

Any now known or later developed volume rendering may be used. For example, projection or surface rendering is used. In projection rendering, alpha blending, average, minimum, maximum, or other functions may provide data for the rendered image along each of a plurality of ray lines or projections through the volume. Different parameters may be used for rendering. For example, the view direction determines the perspective relative to the volume for rendering. Diverging or parallel ray lines may be used for projection. The transfer function for converting luminance or other data into display values may vary depending on the type or desired qualities of the rendering. Sampling rate, sampling variation, irregular volume of interest, and/or clipping may determine data to be used for rendering. Segmentation may determine another portion of the volume to be or not to be rendered. Opacity settings may determine the relative contribution of data. Other rendering parameters, such as shading or light sourcing, may alter relative contribution of one datum to other data. The rendering uses the data representing a three-dimensional volume to generate a two-dimensional representation of the volume.

In act 24, the two-dimensional representations are combined. Any combination may be provided, such as averaging or maximum intensity selection. The representations are aligned based on known geometric relationship or calculated alignment. For calculated alignment, the data of each dataset or each representation are compared to identify a translation and/or rotation providing the best or a sufficient fit. Once aligned, the data is combined into a combined representation. The combined representation is a single view of the volume.

In act 26, a modification is applied. The rendering and/or dataset are modified and acts 22 and 24 are repeated. For example, different color mapping is selected. As another example, one or more of the renderings or datasets is masked or limited (data stripping). Multiple modifications may be made. The modifications may be to both renderings or only one. The repetition may include re-rendering only one representation or both.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for volume rendering data in medical diagnostic imaging, the system comprising:
    a memory operable to store at least one dataset representing a three-dimensional volume, each of the at least one dataset being from a same imaging mode;
    a processor operable to volume render first and second two-dimensional representations of the volume from the at least one dataset, and operable to combine the first and second two-dimensional representations into a combined two-dimensional representation; and a display operable to display the combined two-dimensional representation as an image;

wherein (1) the at least one dataset comprises first and second data sets from the same imaging mode with different processing, (2) the first and second two-dimensional representations are rendered differently, or (3) a combination of (1) and (2).

2. The system of claim 1 wherein the at least one dataset comprises the first and second datasets from the same imaging mode with different processing, the same imaging mode comprises B-mode, parametric imaging mode, or color Doppler mode.

3. The system of claim 2 wherein the same imaging mode comprises color Doppler mode and the different processing comprises velocity and power processing.

4. The system of claim 2 wherein the same imaging mode comprise color Doppler mode or parametric imaging mode and the different processing comprises different color mapping.

5. The system of claim 1 wherein the first and second two-dimensional representations are rendered differently, the first being a function of opacity rendering and the second being a function of maximum intensity projection rendering.

6. The system of claim 5 wherein the same imaging mode comprises B-mode.

7. The system of claim 1 wherein the processor is operable to apply volume manipulation for the first representation independent of the second representation.

8. The system of claim 1 wherein the at least one dataset comprises the first and second datasets from the same imaging mode, the first and second datasets formed from different scans of a patient.

9. The system of claim 1 wherein the at least one dataset comprises the first and second datasets from the same imaging mode, the first and second datasets formed by different processing of a same scan of a patient.

10. A method for volume rendering data in medical diagnostic imaging, the method comprising:

rendering a first three-dimensional representation from a first dataset of b-mode or flow mode type of ultrasound data;

rendering a second three-dimensional representation from the first or a second dataset of b-mode or flow mode ultrasound data, both the first and second three-dimensional representations rendered from a same one of the b-mode or flow mode types, wherein rendering the second three-dimensional representation comprises rendering from the second dataset, the second data set from a different scan than the first dataset;

and combining the first and second three-dimensional representations.

11. The method of claim 10 wherein rendering the first and second three-dimensional representations comprises rendering from b-mode type of ultrasound data, wherein the rendering the first three-dimensional representation comprises opacity rendering, and wherein the rendering the second three-dimensional representation comprises surface or maximum intensity projection rendering.

12. The method of claim 10 wherein rendering the first and second three-dimensional representations comprises rendering from flow mode type of ultrasound data, wherein the rendering the first three-dimensional representation comprises rendering from velocity estimates, and wherein rendering the second three-dimensional representation comprises rendering from power estimates, the velocity estimates mapped with a different color map than the power estimates.

13. The method of claim 10 wherein rendering the second three-dimensional representation comprises rendering from the first dataset.

14. The method of claim 10 wherein rendering the second three-dimensional representation comprises rendering from the second dataset, the second data set from a same scan than the first dataset and with different processing than the first dataset.

15. The method of claim 10 further comprising:

applying a modification to the rendering, the second dataset, or both; and repeating the rendering of the second three-dimensional representation as a function of the modification.

16. The method of claim 15 wherein the modification comprises colorization, data stripping, or both.

17. In a computer readable storage medium having stored therein data representing instructions executable by a programmed processor for volume rendering data in medical diagnostic imaging, the storage medium comprising instructions for:

separately rendering from data of a single ultrasound mode, each separate rendering having different information from the data being relatively enhanced, wherein the data comprises different data sets with the different information, the rendering from the different datasets provides the relative enhancement;

and combining the separate renderings into a single view.

18. The instructions of claim 17 wherein the data comprises a single dataset where differences in rendering provide the relative enhancement.

* * * * *